(12) United States Patent
Clarke

(10) Patent No.: US 9,089,397 B2
(45) Date of Patent: Jul. 28, 2015

(54) IRIS SHIELD

(71) Applicant: Gerald Paul Clarke, Menasha, WI (US)

(72) Inventor: Gerald Paul Clarke, Menasha, WI (US)

(*) Notice: Subject to any disclaimer, the term of this patent is extended or adjusted under 35 U.S.C. 154(b) by 299 days.

(21) Appl. No.: 13/632,271

(22) Filed: Oct. 1, 2012

(65) Prior Publication Data
US 2014/0090653 A1 Apr. 3, 2014

(51) Int. Cl.
*A61B 3/10* (2006.01)
*G02C 11/02* (2006.01)
*G02C 7/00* (2006.01)
*A61B 3/00* (2006.01)
*A61F 9/007* (2006.01)
*A61F 9/04* (2006.01)
*A61F 9/00* (2006.01)

(52) U.S. Cl.
CPC . *A61F 9/007* (2013.01); *A61F 9/04* (2013.01); *A61F 9/0017* (2013.01); *A61F 9/00736* (2013.01); *A61F 2250/0059* (2013.01)

(58) Field of Classification Search
CPC ........ A61B 3/103; A61B 3/135; A61B 3/024; A61B 3/1015; A61B 3/107; G02C 7/04; G02C 7/08; G02C 5/00; G02C 7/16; G02C 11/08; G02C 5/006
USPC ......... 351/214, 200, 205, 222, 41, 45, 46, 52, 351/62–63, 159.02, 159.04, 159.1, 159.18, 351/159.78, 178, 246, 247
See application file for complete search history.

(56) References Cited

U.S. PATENT DOCUMENTS

| | | |
|---|---|---|
| 3,490,455 A | 1/1970 | Illig |
| 3,991,426 A | 11/1976 | Flom et al. |
| 4,782,820 A | 11/1988 | Woods |
| 5,021,057 A | 6/1991 | Byrne, Jr. |
| 5,163,419 A | 11/1992 | Goldman |
| 5,174,279 A | 12/1992 | Cobo et al. |
| 5,267,553 A | 12/1993 | Graether |
| 5,318,011 A | 6/1994 | Federman et al. |
| 5,374,272 A | 12/1994 | Arpa et al. |
| 5,824,086 A | 10/1998 | Silvestrini |
| 5,951,565 A | 9/1999 | Freeman |
| 6,228,093 B1 | 5/2001 | Tomalla |
| 2006/0235428 A1* | 10/2006 | Silvestrini ..................... 606/107 |

(Continued)

OTHER PUBLICATIONS

Uday Devgan, Management of iris prolapse in cataract surgery, The technique of equalizing pressure gradients, Ocular Surgery News, Oct. 15, 2006, Article printed Sep. 16, 2012, 4 pages, Ocular Surgery News U.S. Edition.

*Primary Examiner* — Dwayne A Pinkney
(74) *Attorney, Agent, or Firm* — Thomas D. Wilhelm; Wilhelm Law, S.C.

(57) ABSTRACT

Apparatus and methods for preventing prolapse of iris tissue through a surgical opening in the eye during an ophthalmic surgery. A flexible biocompatible polymeric shield is inserted into the anterior chamber of the eye, placed in position overlying the iris adjacent a surgical opening into the anterior chamber and is thus between the iris tissue and the surgical opening. As pressure inside the anterior chamber increases during the surgery, anterior movement of the iris toward any surgical opening in response to such pressure, also moves the shield anteriorly, such that the shield remains between the iris and the surgical opening. Thus, the shield blocks the surgical opening and prevents movement of eye material to and through the surgical opening. The surgical opening can still be accessed by surgical tools and materials from outside the eye by inserting such articles through the surgical opening and pushing such articles past the shield.

33 Claims, 11 Drawing Sheets

(56) References Cited

U.S. PATENT DOCUMENTS

| | | |
|---|---|---|
| 2008/0269888 A1 | 10/2008 | Malyugin |
| 2008/0275461 A1 | 11/2008 | Nallakrishnan |
| 2010/0076270 A1 | 3/2010 | Merriam |
| 2012/0136322 A1 | 5/2012 | Alster et al. |

\* cited by examiner

IRIS SHIELD

BACKGROUND OF THE INVENTION

This invention relates to ophthalmic surgeries performed on the eye. The invention relates specifically to such surgeries where an increased pressure is developed inside the eye enclosure. Such surgeries include, for example and without limitation, cataract surgery, vitrectomy, glaucoma procedures, and other procedures undertaken behind the iris.

During such surgeries, one or more surgical openings are created in the anterior portion of the eye for the purpose of inserting, into the eye, various surgical instruments, as well as fluids and other assisting items which are used in the surgical procedure or which are temporarily inserted into the eye during the procedure, or which are inserted for the purpose of leaving such item in the eye as part of the surgical procedure. Such surgical openings are commonly created adjacent, and anterior of, the iris, generally adjacent the outer perimeter of the iris, optionally in the sclera.

During such surgical procedures, it is common to add one or more fluids to the anterior chamber of the eye, and it is common that at least some of such added fluid is positioned behind the iris. The addition of such fluid can cause an increase in the fluid pressure inside the eye.

For example, during cataract surgery, one or more surgical openings may be made adjacent the outer perimeter of, and in front of, the iris. One or more instruments are inserted through the surgical openings, in front of the iris, and manipulated inside the anterior chamber, along with administration of suitable fluids inside the anterior chamber, in removing the original natural lens, and inserting a replacement intraocular lens in its place.

In the alternative, during the surgery, the patient may tense the eyelids, which also raises the pressure inside the eye.

Elements of the iris tissue are relatively thin, and are loosely connected to each other. The iris, as a whole is quite mobile. Accordingly, the iris responds to any such increase in pressure by moving away from the area of relatively greater pressure toward an area of relatively lower pressure.

In addition, the strength of the iris tissue can vary from patient to patient, depending on a number of health-related factors, and/or life style factors, including any drugs, such as sympathetic blockers, which the patient may be using.

Thus, as the pressure inside the anterior chamber increases during the surgical procedure, there is a tendency for the iris is to move away from the increased pressure toward an area of relatively lower pressure. The ambient atmosphere outside the eye is such an area of lower pressure. The surgical opening(s) are made through relatively soft and extensible tissue. Any area of the surgical opening which is not fully occupied by an instrument or other article, or to the extent the surgical opening can be enlarged slightly by the internal pressure inside the anterior chamber, such as by stretching the tissue surrounding the surgical opening, provides a path for the iris tissue to move toward that area of lower pressure outside the eye. Any such movement of the iris tissue outside its normal zone of movement creates abnormal stresses on the iris tissue, and can be damaging to the iris tissue.

The result of such abnormal movement of the iris tissue is the protrusion of iris tissue, commonly referred to as prolapse, through the surgical opening. Such prolapse of iris tissue through the surgical opening creates abnormal stresses in the iris tissue and can, in some cases, result in tearing of the iris tissue.

FIG. 1 shows an example of a generally healthy human eye 2 before a surgical procedure has been initiated. There are no openings in the outer tissue adjacent the anterior chamber. There is no path for prolapse of the iris through the eye enclosure.

FIG. 2 shows the same eye as in FIG. 1, but illustrating such prolapse. FIG. 2 illustrates a surgical opening 3 created through the cornea 4 or sclera 5 adjacent the outer edge of the iris 6. As a result of increased pressure inside the anterior chamber, for example during such surgical procedure, the iris has begun to prolapse through the surgical opening and thus a prolapsed portion 8 of the iris extends outside the eye.

It is desirable to prevent such prolapse, which can damage and/or tear the iris tissue and, even where the prolapsed tissue can be drawn back inside the eye enclosure through the surgical opening, such trauma to the eye can result in the patient experiencing pain during the surgery and the patient may experience excessive glare post-surgery.

Thus, the problem to be solved by the invention is to address such prolapse, either by preventing the occurrence of such prolapse, or by providing remedial measures to reverse such prolapse after the prolapse occurs such that the iris tissue moves back inside the eye enclosure.

A conventional treatment for iris prolapse is to watch for prolapse, and to react to such prolapse when prolapse is observed during the surgical procedure. The conventional reaction to prolapse, once the prolapse is observed, is to maintain the increased pressure in the anterior chamber behind the iris, and to increase the pressure inside the anterior chamber in front of the ins. Such increase in pressure in front of the iris apparently urges the iris tissue which remains inside the eye envelope to move rearwardly inside the eye enclosure, thus drawing the prolapsed tissue back through the surgical opening and inside the eye.

Another conventional treatment is to depress the iris and the intraoptical lens inside the eye when the iris prolapses.

Still another conventional treatment is to place a viscoelastic plug in any surgical opening which is not needed immediately, for the period when the pressure is to be increased in the anterior chamber, and then to remove the viscoelastic plug as part of completing the surgical procedure.

Any tissue which may have been torn in the process of a prolapse may be permanently lost. In addition, any iris tissue which has been exposed to ambient atmosphere in the meantime, has also been exposed to any contaminants in the atmosphere, including any pathogenic bacteria, viruses, and the like with which the prolapsed tissue may have come into contact in the atmosphere. So allowing the prolapse to occur, and then responding to such occurrence, entails additional risk of contamination and/or tissue tearing, including the risk of corresponding complications developing as a result of the surgery.

Thus it would be desirable to provide a proactive method for preventing the occurrence of iris prolapse.

It would further be desirable to prevent the iris tissue from becoming exposed to the ambient environment outside the eye enclosure.

It would be further desirable to, as much as possible, prevent the stress and potential for tearing of iris tissue as a result of increased pressure inside the eye enclosure while performing ophthalmic surgery.

It would be desirable that the device would catch the pupil (inner) edge of the iris and maintain dilation of the pupil allowing for the duration of surgery, thereby assisting visualization of the deeper contents (lens) during surgery.

It would further be desirable to avoid inserting small temporary plugs into the surgical opening, lest such small items become fragmented, or lest such small items be inadvertently left inside the anterior chamber at the end of the surgery.

These and other needs are alleviated, or at least attenuated, by the novel products, systems, and methods, of the invention.

SUMMARY OF THE INVENTION

This invention provides apparatus and methods for preventing prolapse of iris tissue or any other eye tissue through a surgical opening in the cornea or sclera, out of the eye during an ophthalmic surgical procedure. At an early stage of the surgical procedure, a suitable flexible biocompatible polymeric shield is inserted into the anterior chamber of the eye and placed in a position overlying the iris adjacent each of the surgical openings into the anterior chamber and is thus between the iris tissue and any surgical openings. If/when the pressure inside the anterior chamber increases during the surgical procedure, any anterior movement of the iris toward the cornea or sclera, namely toward any such surgical opening in response to such pressure, also lifts the shield anteriorly, such that the shield remains between the iris and the respective surgical openings. Thus, the shield blocks the surgical opening and prevents movement of eye material to and through the surgical opening. Namely, the shield closes off access to the surgical opening from inside the eye. The surgical opening can, of course, still be accessed by surgical tools and materials from outside the eye by inserting such articles through the surgical opening and pushing such articles past the flexible shield.

In a first family of embodiments, the invention comprehends an iris shield configured to temporarily overlie an iris of an eye adjacent a surgical opening which has been made through an anterior portion of such eye during an ophthalmic surgical procedure, whereby the shield prevents prolapse of iris tissue past the iris shield and through such surgical opening during such surgical procedure, the iris shield to be removed prior to completion of such surgical procedure, such ins having a generally annular configuration, including an outer edge and an inner edge, the iris shield comprising a flexible biocompatible polymeric sheet which can be folded lengthwise on itself, the sheet, having an anterior side and a posterior side, an inner edge extremity and an outer edge extremity, and a sheet width of about 1 mm to about 5 mm between the inner edge extremity and the outer edge extremity, the sheet having a first end and a second end, and a length therebetween, the outer edge extremity of the flexible biocompatible polymeric sheet extending along a configuration which can overlie the outer edge of a such iris for which the sheet has been configured, such that the polymeric sheet is between the iris and the surgical opening and extends inwardly toward the inner edge of the iris, thus to shield the iris against prolapse through the surgical opening during the surgical procedure.

In some embodiments, the polymeric sheet has an anterior surface and a posterior surface, and a sheet height is defined between the anterior surface and the posterior surface, the posterior surface being generally free from appendages which might engage the inner edge of such iris.

In some embodiments, the sheet has an anterior surface and a posterior surface, further comprising at least first and second retention flanges, spaced from each other and extending from the posterior surface adjacent the inner edge extremity of the polymeric sheet at one or more angles of from 30 degrees acute to, and projectable onto, the posterior surface of said sheet to 135 degrees obtuse to, and not projectable onto, the posterior surface of the sheet.

In some embodiments, a given retention flange has a length extending from a flange base at the polymeric sheet to a flange distal end remote from the polymeric sheet, the length of the retention flange being less than the width of the sheet adjacent the given retention flange.

In some embodiments, a sheet height is defined between the anterior surface and the posterior surface, and at least one of the retention flanges has a thickness less than the height of the biocompatible polymeric sheet.

In some embodiments, the width of the sheet, between the inner and outer edge extremities, is greater than about 2 mm to about 3 mm.

In some embodiments, the sheet has a shore A durometer hardness of 20 to 75.

In some embodiments, the sheet height is generally uniform across the width of the sheet between the inner edge extremity and the outer edge extremity, and optionally has a sheet height of about 100 microns to about 500 microns.

In some embodiments, the sheet extends radially at least 30 degrees, optionally up to about 350 degrees, such as about an axis of the sheet.

In some embodiments, the inner edge extremity of the sheet generally overlies the inner edge of the iris of an eye for which the shield is configured, when the iris is dilated, such that insertion of the shield into the eye, and engaging the shield with the inner edge of the iris, results in minimal, if any, retraction of the iris, and optionally results in stabilizing the iris against constriction during the surgical procedure.

In some embodiments, the sheet extends along a path selected from annular paths, "V"-shaped paths, and paths configured in shapes of polygons.

In some embodiments, the shield further comprises at least one control element which is used to assist in controlling positioning of the shield relative to the iris at a relatively earlier stage of the surgical procedure and/or to assist in controlling removing the shield from the eye at a relatively later stage of the surgical procedure.

In some embodiments, the at least one control element is an aperture extending through the sheet from the top of the sheet to the bottom of the sheet.

In some embodiments, the aperture is proximate one of the first and second ends of the sheet.

In some embodiments, the sheet, when at rest on an underlying flat supporting surface, has a generally flat top surface which extends from the inner edge extremity to the outer edge extremity.

In a second family of embodiments, the invention comprehends an iris shield configured to temporary overlie an iris of an eye adjacent a surgical opening which has been made through an anterior portion of the eye during an ophthalmic surgical procedure, thereby to prevent prolapse of iris tissue past the iris shield and through the surgical opening during the surgical procedure, the iris shield to be removed prior to completion of the surgical procedure, the iris having a generally annular configuration, including an outer edge and an inner edge, the iris shield comprising an annular flexible biocompatible polymeric sheet which can be folded on itself, the sheet having an inner edge extremity and an outer edge extremity, and a sheet width of about 1 mm to about 5 mm between the inner edge extremity and the outer edge extremity, the outer edge extremity of the flexible biocompatible polymeric sheet extending along a configuration which can overlie the outer edge of a such iris for which the sheet has been configured, such that the polymeric sheet is between the iris and the surgical opening and extends inwardly toward the inner edge of the iris, thus to shield the iris against prolapse through the surgical opening during the surgical procedure.

In some embodiments, the iris shield extends 360 degrees as a closed annulus about an axis of the sheet.

In a third family of embodiments, the invention comprehends a method of treating a living eye during an ophthalmic surgery, the eye having an anterior chamber, and an iris in the anterior chamber, the iris having an outer edge and an inner edge, and a width between the outer edge and the inner edge, the method comprising creating a surgical opening into the anterior chamber of the eye: inserting an iris shield into the anterior chamber through the surgical opening in the anterior chamber; positioning the iris shield over the iris adjacent the surgical opening such that the iris shield overlies a substantial portion of the iris adjacent the surgical opening, the iris shield thus being positioned between the iris and the surgical opening so as to prevent prolapse of iris tissue through the surgical opening during the ophthalmic surgery; performing one or more additional surgical procedures while the iris shield is in such overlying relationship with respect to the iris adjacent the surgical opening; and as part of completing the ophthalmic surgery, displacing the is shield from over the iris and removing the iris shield from the eye.

In some embodiments, the positioning of the iris shield in overlying relationship over the iris includes positioning the iris shield such that the iris shield is overlying the outer edge of the iris adjacent the surgical opening.

In some embodiments, the removing of the iris shield from the eye comprises removing the iris shield through the surgical opening.

In some embodiments, the ophthalmic surgery comprises creating more than one surgical opening, accessible by the iris, into the anterior chamber of the eye, the method including selecting one or more suitable iris shields, and positioning the one or more iris shields such that iris shield material is disposed between the iris and each such surgical opening.

In some embodiments, the one or more additional surgical procedures includes a procedure which raises the pressure inside the anterior chamber of the eye, the iris shield being effective, when such pressure is so raised, to shield the iris from the effect of such increased pressure, sufficient to prevent prolapse of iris tissue out of the eye through a such respective surgical opening in the anterior chamber of the eye.

In some embodiments, the iris shield comprises a sheet having an anterior and a posterior, an inner edge extremity and an outer edge extremity, and first and second retention flanges spaced from each other, each such retention flange extending from a posterior surface of the sheet at the inner edge extremity, at an angle of from 30 degrees acute to, and projectable onto, the posterior surface of the sheet to 135 degrees obtuse to, and not projectable onto, the posterior surface of the sheet, the method further comprising engaging the retention flanges with the inner edge of the iris, the iris shield thus engaging the inner edge of the iris.

In some embodiments, the iris shield prevents the iris from constricting during the surgical procedure, optionally stabilizing the iris against constriction during the ophthalmic surgery.

In some embodiments, the engaging of the retention flanges with the inner edge of the iris does not result in substantial retraction of the iris.

In some embodiments, the iris shield extends about greater than 180 degrees of the circumference of the iris, and may comprise an annular biocompatible polymeric sheet.

In some embodiments, the iris shield overlies at least 75 percent of the width of the iris between the inner edge and the outer edge, including substantially overlying the outer edge of the iris.

In some embodiments, the iris shield is positioned over the iris, and between the surgical opening and enough of that portion of the iris which is proximate the surgical opening to prevent prolapse of iris tissue through the surgical opening.

Figure 1:
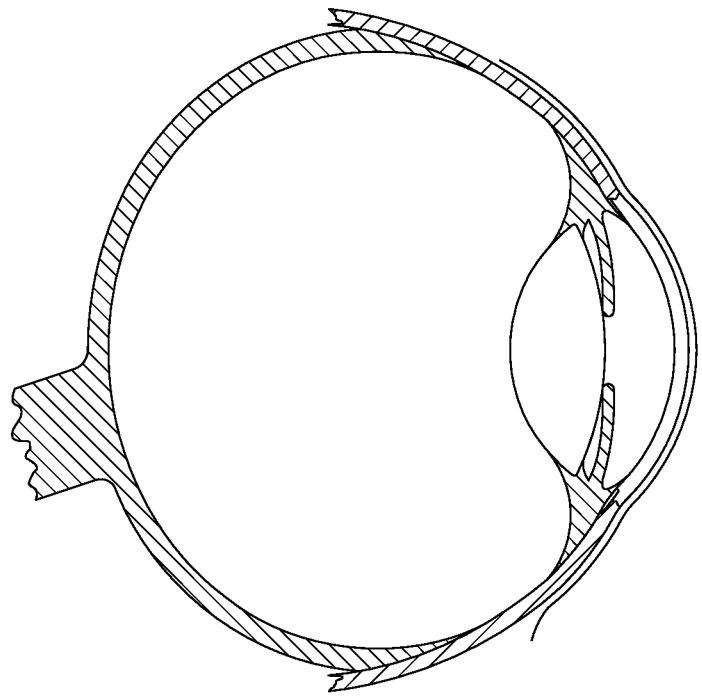
FIG. 1 shows a relatively healthy human eye prior to any performance of ophthalmic surgery.
Figure 2:
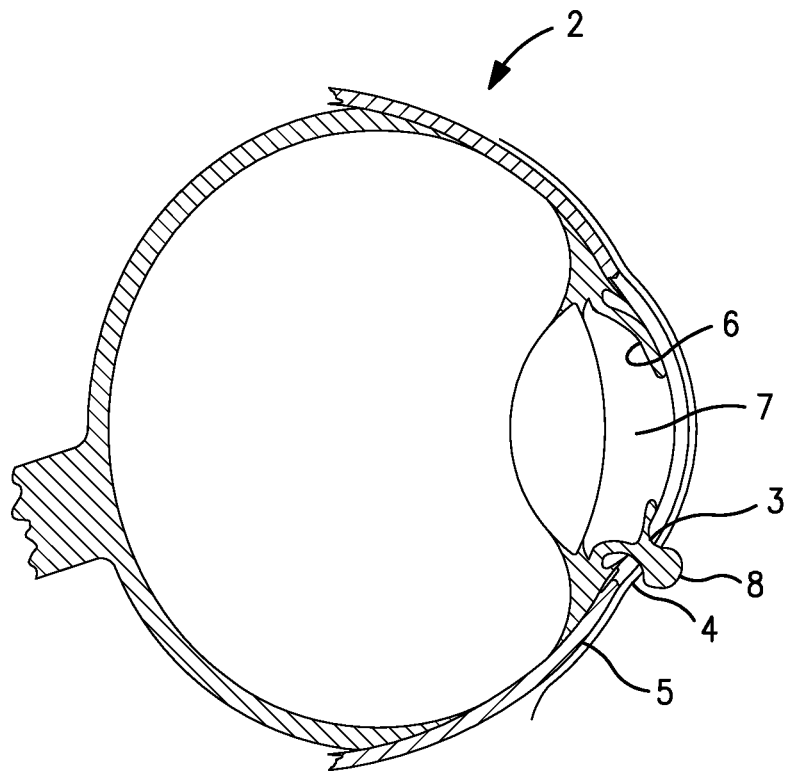
FIG. 2 shows the eye of FIG. 1 with a prolapsed iris after a surgical opening has been created in the eye enclosure and pressure has been increased in the anterior chamber behind the iris.

The invention is not limited in its application to the details of construction, or to the arrangement of the components set forth in the following description or illustrated in the drawings. The invention is capable of other embodiments or of being practiced or carried out in various other ways. Also, it is to be understood that the terminology and phraseology employed herein is for purpose of description and illustration and should not be regarded as limiting. Like reference numerals are used to indicate like components.

DETAILED DESCRIPTION OF THE
ILLUSTRATED EMBODIMENTS

In the invention, a sheet-shaped shield of slightly stiff, biocompatible polymeric material is inserted into the anterior chamber of the eye, through a peripheral corneal or sclera surgical opening, and placed on the iris inside the eye to prevent prolapse of iris tissue outside the eye by adding blocking support to the iris tissue and optionally engaging the inner edge of the iris to, as an additional benefit, prevent constriction of the iris over the pupil.

Figure 3:
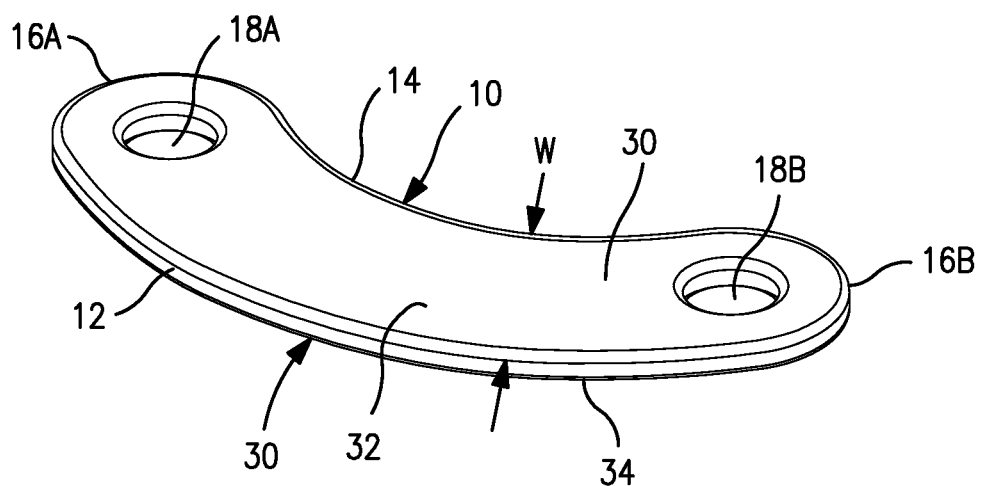
FIG. 3 is a pictorial representation of a simple iris shield of the invention.
Figure 4:
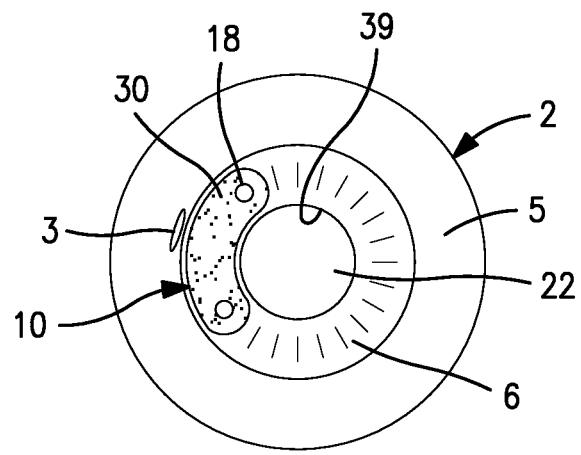
FIG. 4 is a view from the front of an eye, with the iris shield of FIG. 3 installed adjacent a surgical opening in the sclera, the iris shield being between the iris and the outer layers of the eye enclosure.

Referring to the drawings, FIGS. 3 and 4 show a rather simplistic embodiment of the invention. FIG. 3 shows a curved silicone shield 10 which extends 90 degrees about the circumference of an imaginary circle. FIG. 4 shows the shield 10 in use over a portion of the iris during a surgical procedure.

Shield 10 is made of a flexible surgical-grade polymer. The outline of the shield shown in FIGS. 3 and 4 generally conforms, along its length, to the outline of the iris of the human eye, including the outer edge extremity 12 of the shield, the inner edge extremity 14 of the shield, and the width "W" between the inner and outer edge extremities. The first and second ends 16A, 16B of the shield are also curved as the ends connect the inner and outer edge extremities to each other. Apertures 18A, 18B function as control elements for controlling and manipulating the shield and are located inwardly of ends 16A, 16B, generally equidistant from edge extremities 12, 14 and the respective ends 16A, 16B. Such control elements can take a number of forms, including protrusions, or indentations, as well as the apertures illustrated.

FIG. 4 shows a human eye 2 in isolation, with no surrounding tissue being shown. Of course, in a real surgical procedure, the eye is disposed in an eye socket in the face of the patient. However, none of such surrounding tissue is shown in FIG. 4. Thus, the elements of the eye, as visible to casual observation from the front, are the pupil 22, the iris 6, and the white portion of the sclera 5. During surgery, a small surgical opening 3 is created in the front portion of the eye, typically adjacent the outer edge of the iris. Such surgical opening is typically about 2-3 mm in length.

Various preliminary steps may be performed in the surgical procedure of e.g. a cataract removal and replacement, prior to any injection, into the eye, of any material which would increase the internal pressure inside the eye. During the surgical procedure, shield 10 is inserted through the surgical opening, and positioned over the iris adjacent the surgical opening prior to the application of any significant increase in pressure inside the eye enclosure. This shield 10 is inserted before any material is injected into the eye to e.g. fracture a crystallized natural lens which is to be removed and replaced.

Typically, the shield will be folded on itself lengthwise, e.g. along a longitudinal axis, and placed in an injector instrument, such as those used to inject artificial e.g. intraocular lenses, in order to more easily fit through the surgical opening. Using a suitable such insertion tool, the shield is inserted through the surgical opening, and into the eye. Once the shield has passed completely through the surgical opening, the shield is released from the tool and allowed to unfold.

A suitable manipulation tool is then engaged with the shield at one or both of apertures 18A, 18B and used to complete the unfolding of the shield if needed, and to position the unfolded shield over the iris as shown, the shield generally extending in opposing directions from the surgical opening and about the circumference of the iris. As the shield is being positioned in the eye, the length of shield 10 is generally centered on the surgical opening if only one surgical opening has been created. The shield, in its use position as illustrated in FIG. 4, thus provides a protective covering over the iris at and adjacent the surgical opening. Where more than one surgical opening is created in the eye, a shield is selected for use whose length is great enough that the length of the shield can extend past all such surgical openings.

Any increase in pressure inside the eye is commonly transferred to the iris as an outwardly-directed, anteriorly-directed force, thus urging the iris to move outwardly of, anteriorly of, the eye.

Iris tissue is typically quite soft. Where the iris material is sufficiently soft, the iris tissue can thus flow toward any lower pressure at the surgical opening unless such movement is impeded/blocked. With the shield positioned in overlying relationship over the iris as illustrated in FIG. 4, such upwardly, and outwardly, anteriorly-directed force urges the iris against the underside/posterior surface of the shield. Shield 10 receives that force and spreads the force along the length and width of the shield. Since the shield has generally-fixed length, width, and height dimensions, and is not liquidous, thus cannot flow, such upwardly, outwardly, anteriorly-directed force moves the shield, from its rest position overlying the iris, anteriorly against the outer tissues of the eye, such as against the cornea and optionally against a portion of the sclera.

Thus, while shield 10 is quite flexible, and with a generally central portion of the shield adjacent surgical opening 3, the generally limited extensibility of the shield, in the length and width dimensions, does not allow the shield to change shape enough to be forced out the surgical opening. And since the shield is between the iris and the surgical opening and is wide enough to prevent the iris material from circumventing the shield and flowing out the surgical opening, the shield serves as an effective barrier, protecting the iris such that iris material does not flow beyond the shield toward the surgical opening, and thus does not prolapse out the surgical opening.

With the shield in place as shown in FIG. 4, the surgeon then continues the surgery according to conventionally-accepted surgical procedures, with instrument elements, supplies, and/or implant elements being passed into and out of the eye enclosure through the one or more surgical openings, and wherein the shield is between the iris and the instrument elements, supplies, and/or other implant elements. Thus, the shield not only serves to protect the iris from the effects of increases in pressure, the shield also serves as a buffer/shield to prevent, or reduce in extent or severity, direct contact of the instruments, supplies, implant elements, and the like, with the rather delicate iris tissue.

Where more than one surgical opening is made into the eye during the surgical procedure, a second shield may, optionally, be placed adjacent the second surgical opening. In the alternative, a longer such shield may be selected as the sole shield used, whereby the single shield extends along and well past all of the surgical openings providing prolapse protection to the iris at all of the surgical openings.

Once the pressure inside the anterior chamber of the eye returns to more normal pressures, and where the pressure is expected to not again increase to a high enough level to facilitate prolapse of iris tissue, shield 10 is removed through the surgical opening, again using a suitable instrument to manipulate the shield by interaction with the edges of apertures 18A, 18B.

Shield 10 can be inserted into the eye any time after a surgical opening is created, with commonly used micro forceps, or with a commonly used injector system wherein the shield may be folded lengthwise on itself, e.g. about its longitudinal axis. After the shield has been inserted through the surgical opening and into the anterior chamber, forceps are engaged in apertures 18A and/or 18B and thus used to manipulate the shield into place over the iris. Once the remaining steps in the surgical procedure have been completed, the shield is then removed using a small hook commonly known as a Connor Wand, a Sinskey Hook, or the like.

Once shield 10 has been removed from the eye, through the surgical opening, the surgery again proceeds and/or concludes according to conventionally-accepted surgical procedures.

Figure 5:
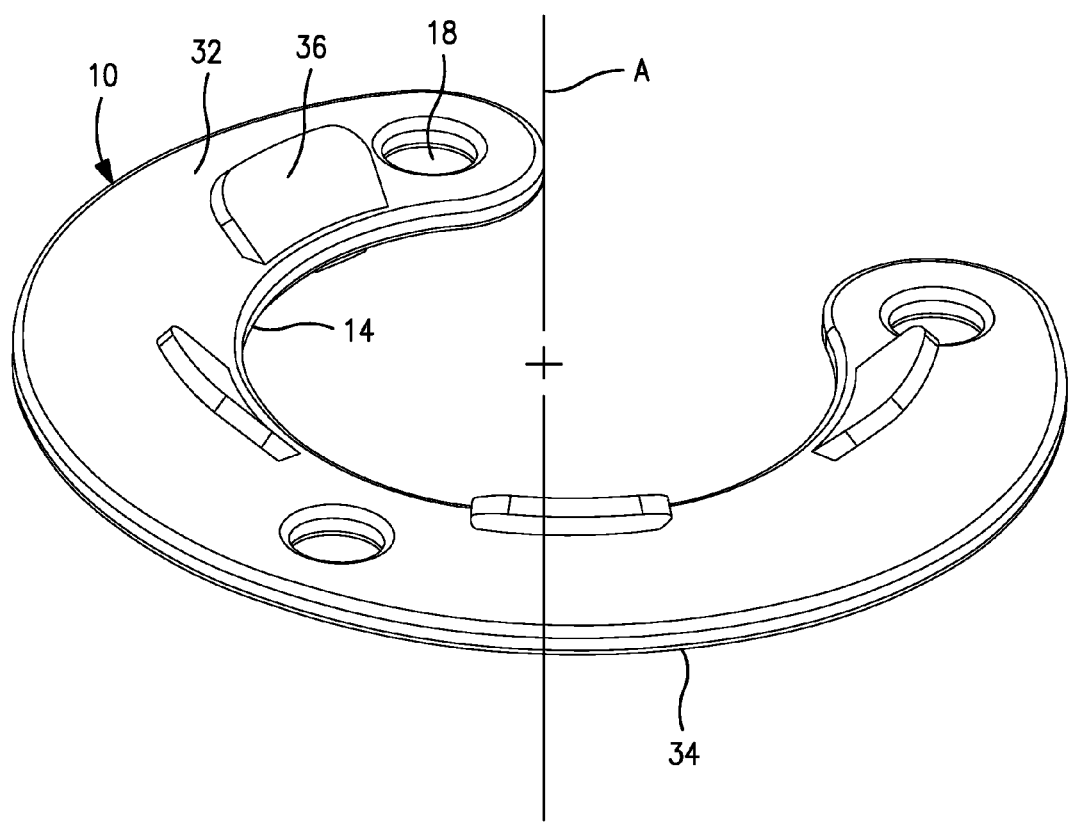
FIG. 5 is a pictorial view of a second embodiment of iris shields of the invention.
Figure 6:
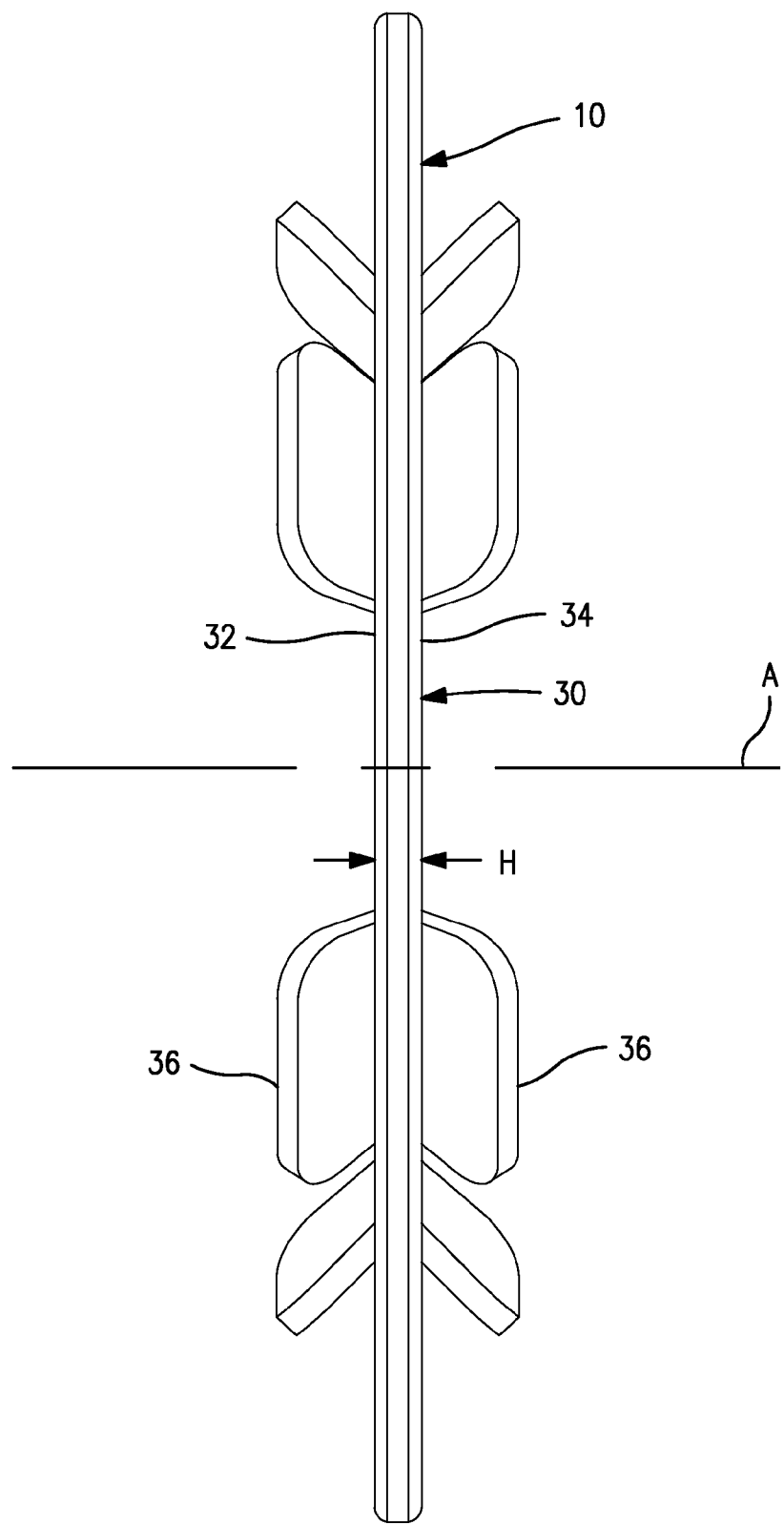
FIG. 6 is an edge view of the iris shield of FIG. 5.
Figure 7:
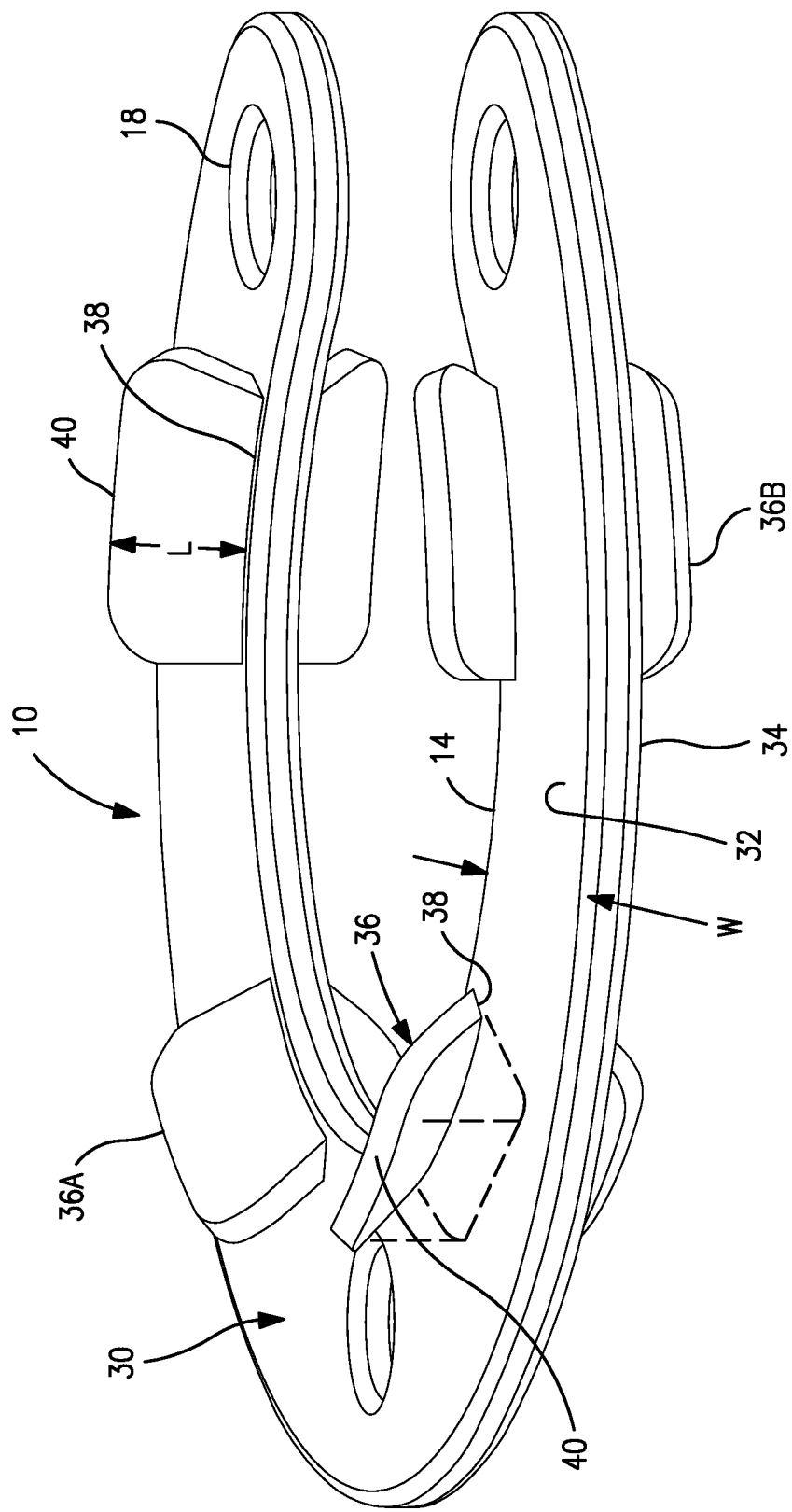
FIG. 7 is another pictorial view of the embodiment of iris shields illustrated in FIGS. 5 and 6.

FIGS. 5, 6, and 7 illustrate a second embodiment of ins shields of the invention. The shield of FIGS. 5-7 differs in at least 3 substantial ways from the shield of FIGS. 3-4.

First, while both shields are generally circular in shape, the shield of FIGS. 3-4 extends about 90 degrees about a circumference of a such circle while the shield of FIGS. 5-7 extends about 270 degrees about the circumference of the circle, e.g. about central axis "A" of the shield. Thus, the shield of FIGS. 5-7, in use, nominally covers about 3 times as much surface area of the iris as is covered by the shield of FIGS. 3-4.

Second, the shield 10 of FIGS. 3-4 is a flat, smooth sheet 30 on both its top surface 32 and its bottom surface 34. By contrast, the shield of FIGS. 5-7 has a series of retention flanges 36. A given retention flange 36 extends, from a flange base 38 adjacent the inner edge extremity 14 of the sheet 30 at the top or bottom surface of sheet, along a length "L" of the flange, to a distal end 40 of the flange remote from the flange base. In the embodiments of FIGS. 5-7, the lengths "L" of the retention flanges are less than the width "W" of the shield.

In the embodiments of FIGS. 5-7, four retention flanges 36A are spaced from each other along the length of the top surface of the sheet, and another four retention flanges 36B are spaced from each other along the length of the bottom surface of the sheet. Flanges can extend at any angle to the respective surface of the sheet, from about 30 degrees acute angle, including a perpendicular angle, to an obtuse angle of about 135 degrees, e.g. in increments of about 1 degree, with respect to the respective surface of the sheet. In FIGS. 5-7, each such flange 36 extends at an acute angle of about 35 degrees to the respective top or bottom surface of the sheet.

In typical embodiments, the entirety of each acute angle flange can be projected onto the sheet as illustrated with one of the flanges in dashed outline on the left side of FIG. 7. Typically, the acute angle flanges which overlie the sheet, or underlie the sheet, are shorter in length "L" than the width "W" of the sheet, whereby the outline of a given acute-angle flange can be projected onto the sheet, at a perpendicular angle to the sheet. By contrast, obtuse angle flanges typically cannot be projected onto the sheet unless the base 38 of the respective flange is located away from inner edge extremity 14 of the sheet, toward outer edge extremity 12 of the sheet.

The purpose of retention flanges 36 is to engage and hold the inner edge 39 of the iris (FIG. 10), thus to control, prevent movement of the inner edge of the iris. With suitable stiffness in the material of sheet 30, the shield holds its shape over the iris, thus generally holding the iris immobile during certain portions of the surgical procedure, preventing the iris from constricting such that the iris cannot constrict over the pupil of the eye and thus impede visualization of rearwardly-disposed portions of the anterior chamber, where the lens is located, by the attending surgeon. Typically, and as shown in FIG. 5-7, but not necessarily, all of the retention flanges on a given shield will bear the same angularity with respect to sheet 30.

In use inside the anterior chamber of an eye, flanges 36 extend posteriorly from the bottom/posterior surface of the sheet in order to engage the inner edge of the iris. Thus, any flanges which extend anteriorly from sheet 30 are extraneous to a given surgical procedure.

However, by having flanges extending from both the anterior surface and the posterior surface of the sheet inside the eye, the shield is insensitive to top-or-bottom orientation of the shield when the shield is inserted into the eye. Such lack of sensitivity of the shield to orientation allows the surgeon to insert the shield without concern with potentially needing to invert the shield after the shield has been inserted. Thus, the shields represented by FIGS. 5-7, having retention flanges extending from both the top surface of the sheet and the bottom surface of the sheet, present suitable retention flange orientation irrespective of which surface of the shield presents itself to the iris when the shield emerges from the insertion tool inside the anterior chamber.

Height "H" of sheet 30, between the top surface and the bottom surface, is about 100 microns to about 500 microns, optionally about 200 microns to about 400 microns yet further optionally about 350 microns. The thicknesses of the retention flanges is about 100 microns to about 300 microns, optionally about 200 microns to about 300 microns, with the thicknesses of the flanges being optionally less than the height of the sheet 30 to which such flanges are attached.

The height of sheet 30 is driven by a number of factors including, without limitation, the hardness of the sheet material, the width of the sheet, the flexibility of the sheet, foldability of the sheet, rigidity of the sheet, strength of the sheet, and the like. The thickness of a retention flange 36 is driven by flexibility of the flange, strength of the flange, the ability of the flange to conform to the surface of the iris or the surface of the overlying cornea or sclera, and the like under pressure which typically exists in the eye during eye surgical procedures. In general, in fulfilling their functions relative to the iris, inside the anterior chamber, flanges 36 have a greater requirement to be foldable, flexible, than does sheet 30.

Retention flanges 36 may be shaped as desired, such as rectangular, scalloped, trapezoids, ovals, or the like, and are spaced from each other.

The third way the shield of FIGS. 5-7 differs from the shield of FIGS. 3-4 is that, while the shield 10 of FIGS. 3-4 has two apertures 18, the shield of FIGS. 5-7 has 3 apertures 18. The third aperture in the longer sheet provides an additional location for engaging the shield and manipulating the shield into position over the iris, and for engaging the shield and removing the shield from the eye through the surgical opening. The number of apertures can be selected and specified by the designer of a such shield as greater than 3 apertures, or less than two apertures, in accord with specific needs contemplated for the particular shield.

A given shield 10 of the invention, both sheet 30 and any flanges 36, is typically made of a single material, and sheet 30 and flanges 36 are typically fabricated simultaneously as a single piece. A typical fabrication process is injection or other type of molding of a fluid polymeric composition, followed by cooling, solidification to fix the shield material in the desired configuration.

Shields 10 can be made from a variety of polymeric materials, such as various ones of the silicones, acrylics, and collamers. Specific compositions, and combinations of compositions, can be selected by those skilled in the art based on known physical properties, and biocompatibilities of materials of interest. Conventional biocompatible additive packages can be used as desired.

Especially height of sheet 30 is at least in part driven by strength and stiffness of the material once fabricated into the sheet form. Two non-limiting examples of suitable such material for use in shields of the invention are NuSil Med-4950 and NuSil Med 4970 silicones, having 50 Shore A and 70 Shore A hardnesses, respectively, both available from NuSil Technology, Carpinteria, Calif. Other conventionally available materials may be selected for other hardness specifications.

Typical hardness of the sheet 30, after fabrication, is about 20-75 Shore A, optionally about 20-40 Shore A.

A typical shield of the invention, as that shown in FIGS. 5-7, has an outer diameter of about 12 mm to about 13 mm. A shield having such outer diameter can be comfortably fitted into, and will generally extend across substantially the entirety of, the anterior chamber of an adult human eye. Thus, where the shield extends at least half way around the anterior chamber, e.g. at least 180 degrees about the anterior chamber, opposing sides of the shield are generally positioned proximate or against the outer perimeter of the anterior chamber. Given an appropriate stiffness of the shield, such that the shield is not easily compressed inwardly toward its own central axis inside the anterior chamber by ambient pressures exerted inside the anterior chamber during the surgical procedure, opposing sides of the shield tend to center the shield about the central axis of the anterior chamber as defined between the front of the eye and the back of the eye. Thus, such shield, having a length corresponding to at least 180 degree progression about the central axis of the shield, assists the surgeon in his steps of positioning the shield uniformly about the iris such that the shield is positioned to cover as much of the iris as possible along the circumferential length of the shield, with specific attention to covering as much as possible of the iris tissue which is adjacent the surgical opening. In general, the surgeon positions the shield such that, to the extent reasonably possible, the outer edge extremity of the shield overlies that portion of the outer edge of the iris which is adjacent a surgical opening, and in addition, as much as possible for a given shield, such that the shield overlies that portion of the iris which extends radially from the surgical opening.

Where more than one surgical opening has been created in the eye, the surgeon positions the shield so as to so protect the iris adjacent all, or as many as possible, of the surgical openings. Specifically, where more than one surgical opening has been created, the surgeon selects a shield which has a length great enough to extend past each of the surgical openings.

Thus, for a surgical procedure where only one surgical opening will be created, a simple shield such as the one shown in FIGS. 3-4, extending only 90 degrees about the circumference of the anterior chamber, may be sufficient, with or without retention flanges 36.

Where two or more surgical openings will be created, typically opposite each other about the edge of the cornea or sclera, a shield is selected having a length which extends at least past both surgical openings. Thus, a shield extending about 270 degrees of the circumference of the anterior chamber may be selected. In some cases, such as where there may be unknown steps required during the surgical procedure, which may suggest an unknown number of surgical openings to perform such steps, a full-circle shield may be selected, namely a shield which extends about the full 360 degree circumference of the anterior chamber; or a substantially full circle shield having two ends but extending up to less than 360 degrees, e.g. about 350 degrees, may be selected.

Prior to beginning a surgical procedure, the surgeon will already know measurements of the patient's eye and will have secured a suitable supply of shields of the size or sizes expected to be needed for the specific patient and/or surgical procedure. Such size may be greater than 12-13 mm, or may be less than 12-13 mm, depending on the measurements of the respective patient.

Thus, a manufacturer of such shields for use in human eyes may typically fabricate such shields in at least three outer diameter sizes, for example, the average 12-13 mm size outer diameter, one slightly larger than 12-13 mm, such as 14-15 mm, and one slightly smaller than 12-13 mm, such as 10-11 mm.

The width "W" of the shield, between the outer edge extremity and the inner edge extremity, should be great enough to cover, and provide a shielding effect, to enough of the iris that any portion of the width of the iris which is not overlain by the shield is not susceptible to moving to and/or through the surgical opening. Typical width "W" of an effective such shield is about 1 mm to about 3 mm, optionally about 2 mm to about 3 mm, optionally about 22 mm to about 2.6 mm, optionally about 2.4 mm.

Given the above discussions of the outer diameter of the shield and the width of the shield, the inner diameter of the shield can be calculated to be about 6 mm to about 9 mm, optionally 6 mm to about 7 mm, optionally about 6.2 mm.

A shield of the invention is used only during the surgical procedure. The shield is removed as one of the latter steps in the surgery. The shield is not left in the eye after the surgical procedure has been completed.

Figure 8:
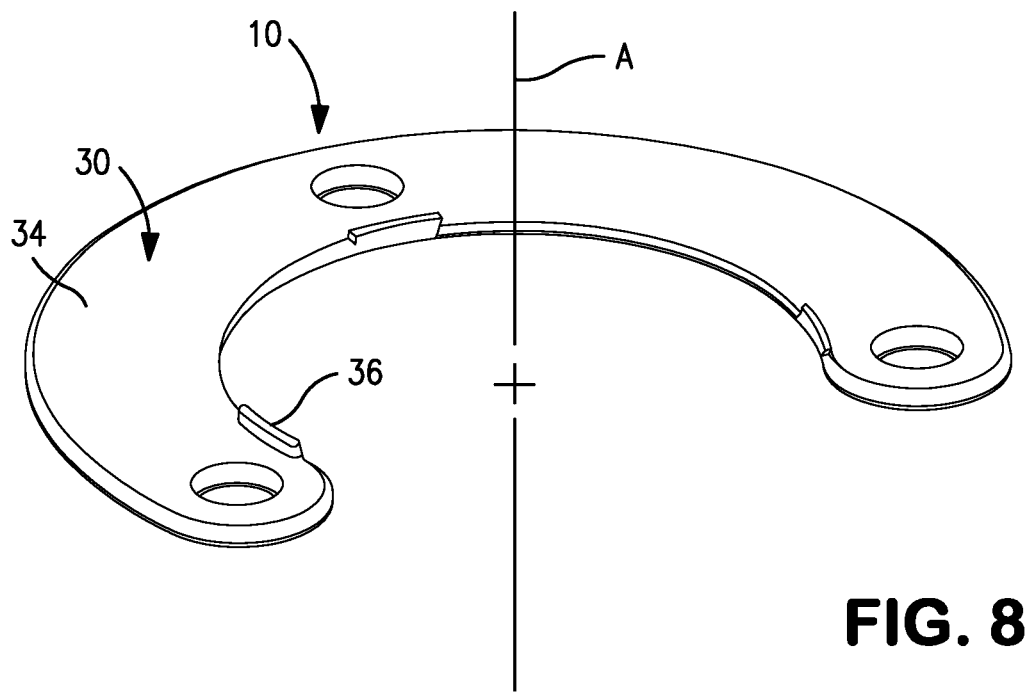
FIG. 8 is a pictorial view of a third embodiment of iris shields of the invention.

Returning now to the drawings, FIG. 8 shows a pictorial view of a shield which extends 220 degrees about its central axis "A". Because this embodiment of the shield extends more than 180 degrees about the central axis, sufficiently stiff shields represented in FIG. 8 have the above tendency to assist the surgeon in positioning the shield in the anterior chamber. Still referring to the embodiment shown in FIG. 8, retention flanges 36 extend perpendicularly upwardly from sheet 30. Given that the shield is designed to overlie the iris, given that flanges 36 must extend toward the interior of the eye to so engage the inner edge of the iris, the surface seen in FIG. 8 is bottom surface 34 of the shield.

As a review, FIGS. 5-7 show retention flanges 36 at acute angles relative to sheet 30; and FIG. 8 shows retention flanges 36 perpendicular to sheet 30.

Figure 9:
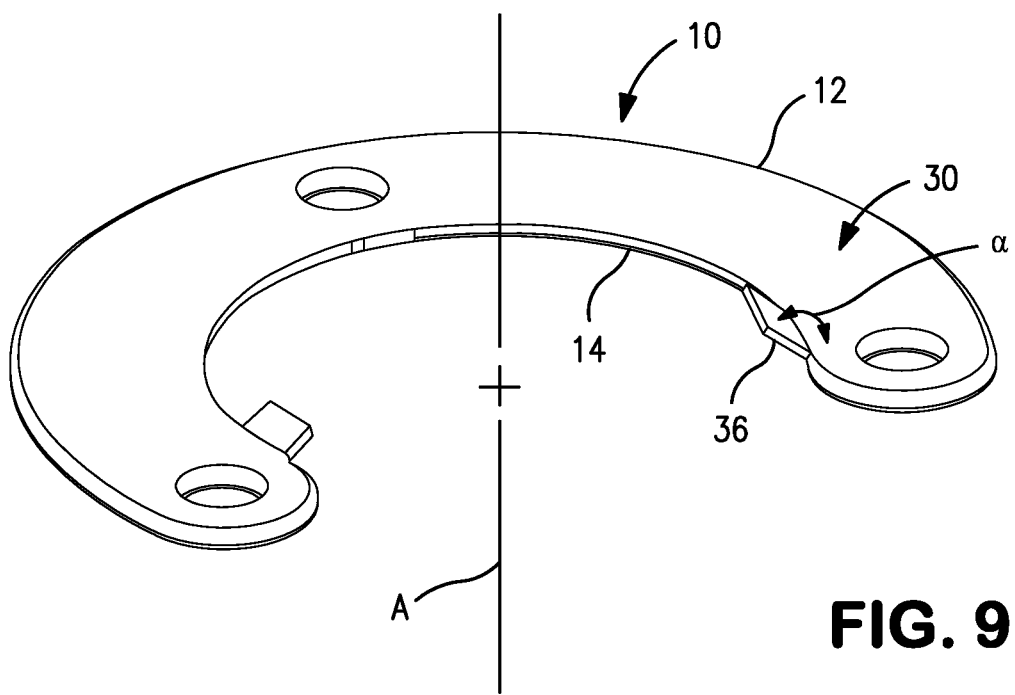
FIG. 9 is a pictorial view of an embodiment like that of FIG. 8, except that the retention flanges are at obtuse angles with respect to the shield sheet.

FIG. 9 illustrates an embodiment of shield 30 where retention flanges 36 are obtuse to sheet 30, extending away from both the outer edge extremity and the inner edge extremity, of the sheet, and toward central axis "A" of the shield. Measured from the top surface of sheet 30, flanges 36 extend at obtuse angles α of about 135 degrees to sheet 30.

Figure 10:
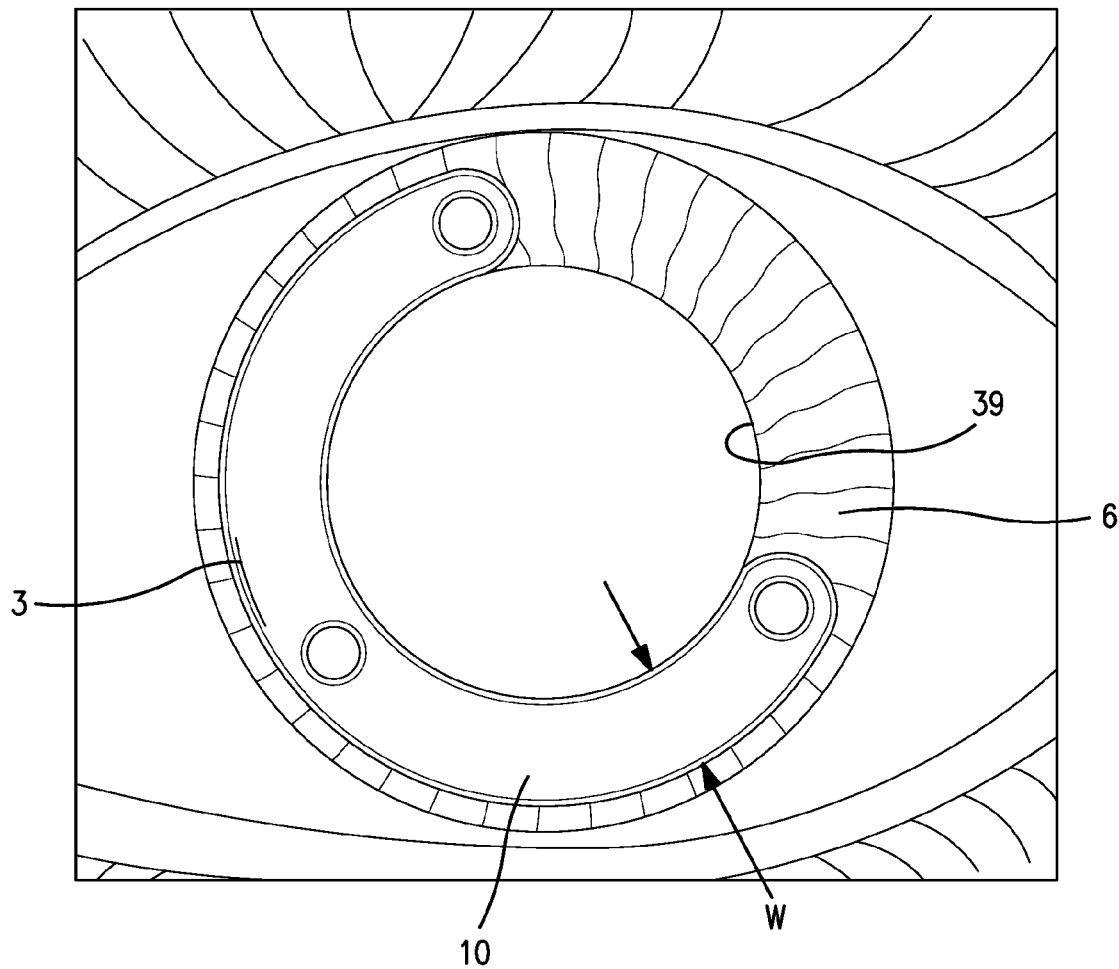
FIG. 10 shows a front view of the eye, with the iris fully dilated, showing the iris shield of FIG. 8 in place inside the anterior chamber, in its shielding position over the iris, between the iris and the eye enclosure tissue.

FIG. 10 shows a photographic representation of a fully dilated eye with the shield 10 of FIG. 8 in place over the dilated iris. The width "W" of the shield generally corresponds with the dilated width of the iris. The width of the shield adjacent surgical opening 3 generally overlies the entirety of the width of the iris, thus protecting substantially all of the width of the iris adjacent opening 3 from prolapse through opening 3.

Figure 11:
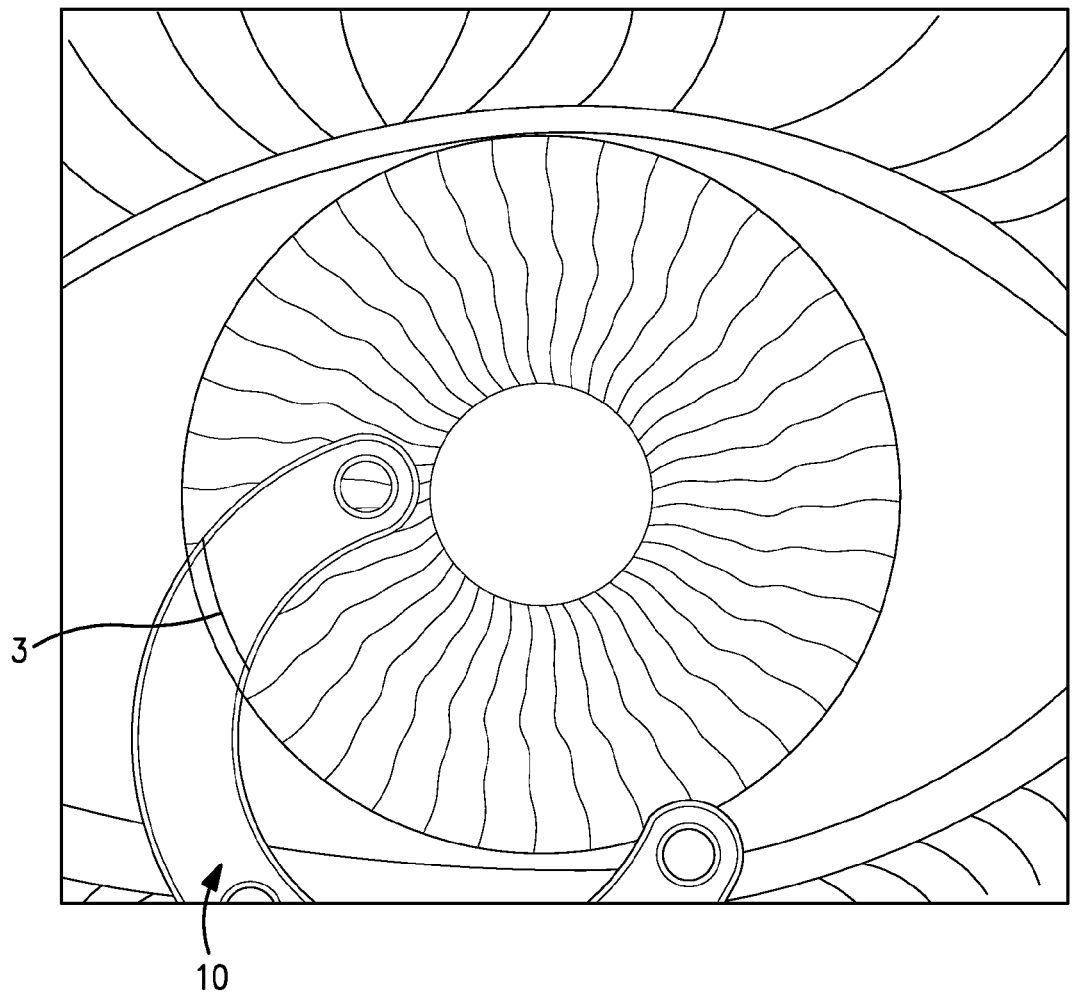
FIG. 11 is a front view of an eye as in FIG. 10, wherein the eye is no longer dilated, showing the iris shield being removed from the anterior chamber of the eye through the surgical opening.

FIG. 11 shows a photograph representation of the eye as in FIG. 10, but not dilated, where the width of the shield is substantially less than the width of the iris. The surgeon is in the process of removing the shield from the anterior chamber, optionally inserting the shield into the anterior chamber unfolded, through surgical opening 3. For the removal process, forceps, not shown, are used to pull and otherwise manipulate the shield through the opening and out of the eye.

In the illustrations shown in FIGS. 10 and 11, shield 10 has been inverted from the image shown in FIG. 8 such that retention flanges 36 extend away from the viewer on the non-visible bottom surface of the shield, and thus are not seen in FIGS. 10 and 11.

Figure 12:
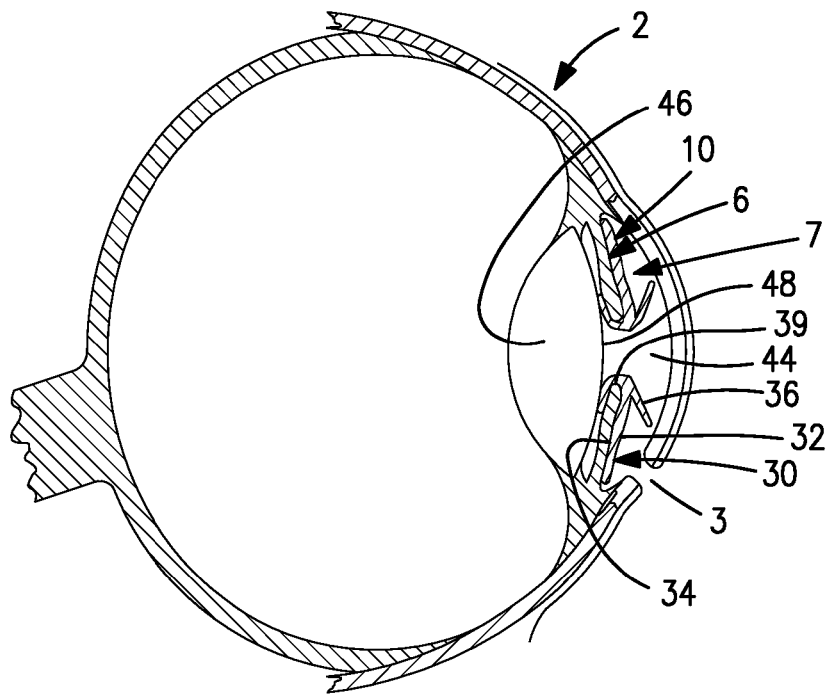
FIG. 12 shows a cross-section of an eye before any surgery-induced increase in pressure inside the anterior chamber, with an iris shield of FIGS. 5-7 in place overlying the iris and between the iris and the anterior tissue which forms part of the eye enclosure.
Figure 13:
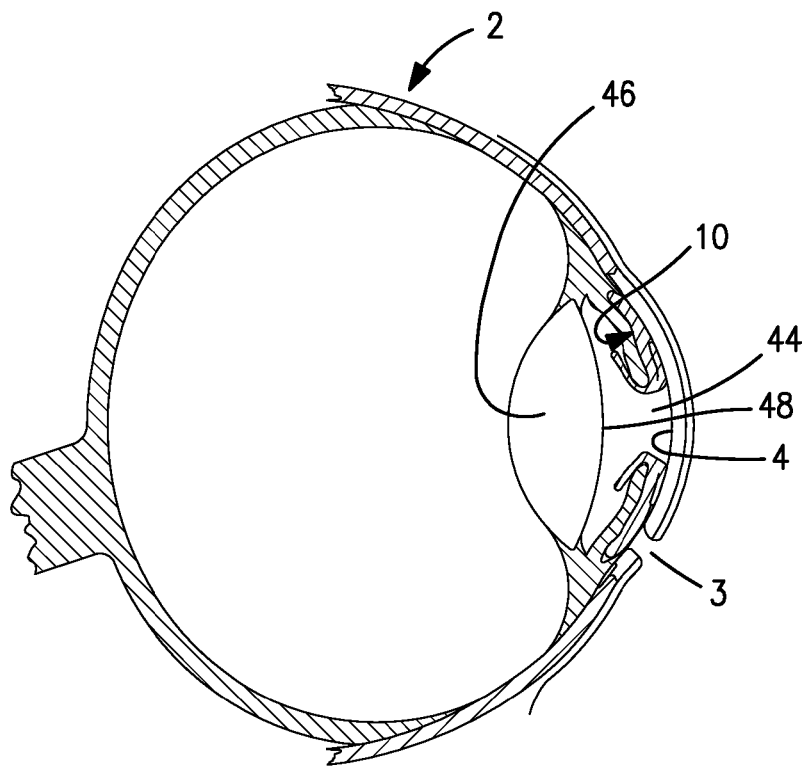
FIG. 13 shows a cross-section of the eye of FIG. 12 after the pressure inside the anterior chamber has been increased, showing the iris shield performing its shielding function between the iris and the surgical opening.

FIGS. 12 and 13 show cross-sections of an eye 2 where a surgical opening 3 has been created, and where shield 10 has been inserted into anterior chamber 7 and positioned in a location overlying iris 6. In FIG. 12, the pressure inside the anterior chamber is generally equalized between the front portion 44 of the anterior chamber, in front of the iris, and the rear portion 46 of the anterior chamber to the rear of the iris, such that the iris is positioned in its normal, undisturbed, location adjacent lens 48.

As shown in FIG. 12, shield 10 has retention flanges 36 extending from both the top surface 32 of sheet 30, and the bottom surface 34. As seen in FIGS. 12 and 13, the shield has been manipulated about the inner edge of the iris such that the retention flanges on the bottom surface of the shield have been worked under the inner edge of the iris, thus to retain the shield firmly in its shielding position overlying the iris. As a further benefit of the use of retention flanges, the flanges prevent the iris from constricting while the shield is so in place over the iris.

In FIG. 13, the pressure inside the rear portion 46 of the anterior chamber is greater than the pressure in the front portion 44 of the anterior chamber, such that the iris has been pushed upwardly against the cornea 4, including against surgical opening 3. As seen in FIG. 13, shield 10 is between the iris and opening 3, thus temporarily closing off opening 3, temporarily obstructing opening 3, and preventing any prolapse of the iris, or any other material, through the opening.

FIGS. 12 and 13 illustrate the flexibility of flanges 36, such that the flanges on the bottom of the shield generally deflect against the iris, between the lens and the iris, when the pressure is generally equalized between the front and rear portions of the anterior chamber. Similarly, when the pressure gradient occurs between the front and rear portions of the anterior chamber, and the iris moves against the shield, and toward the cornea, the flanges on the top surface of the shield deflect against the top surface of the shield, between the shield and the cornea, thus avoiding having open space between the top surface of the shield and the flanges, through which iris tissue, or other material in the eye, might escape to and through the surgical opening.

Figure 14:
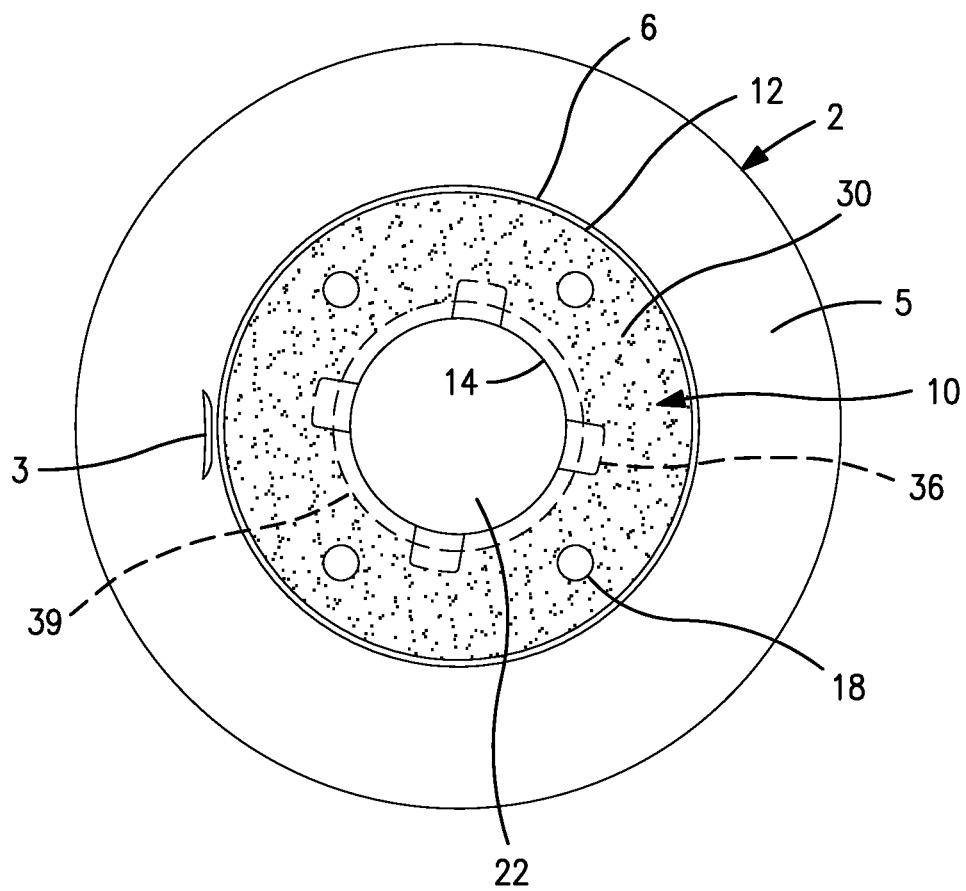
FIG. 14 is a view from the front, of an eye as in FIG. 4, with an iris shield installed, overlying the iris, wherein the iris shield extends about the full circumference of the iris, and is thus a full-circle shield having four retention flanges engaged with the inner edge of the iris.

FIG. 14 shows a front view of the eye of FIGS. 12 and 13, with the shield in place overlying the iris. The flanges underlying sheet 30 are shown in dashed outline, as is the inner edge 39 of the iris. The flanges on the top surface of the sheet have been omitted so the underlying flanges can be seen.

Figure 15:
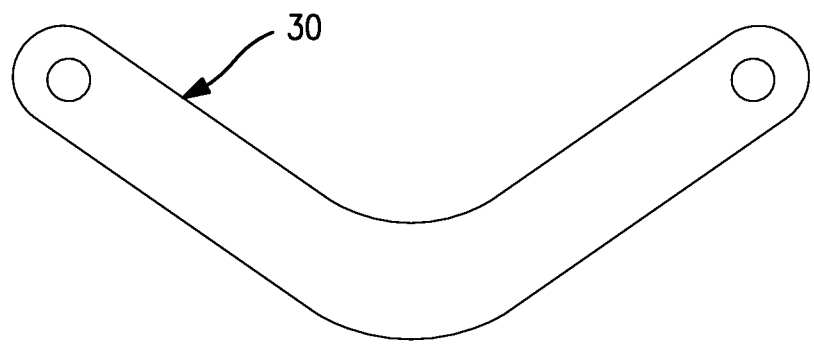
FIG. 15 shows a top view of a fourth iris shield of the invention, in a V-shape.
Figure 16:
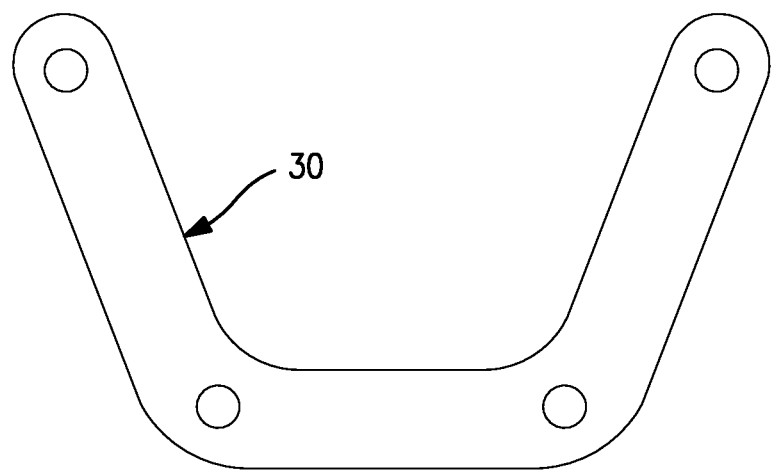
FIG. 16 shows a top view of a fifth iris shield of the invention, in a "polygon"-shape.

FIGS. 15 and 16 show shield sheets 30 which illustrate that sheet 30 need not have a circular configuration. FIG. 15 shows a sheet 30 having a "V"-shaped configuration. FIG. 16 shows a sheet 30 having a straight-sided "U"-shaped configuration, which can also be referred to as an open-ended polygonal configuration. FIGS. 15 and 16 thus illustrate that the sheet can have a wide variety of configurations, though the dimensions of such sheets still have the requirement that the sheet, in use in the eye, must provide the opportunity for the surgeon to position the shield such that the shield presents sufficient shielding material adjacent any surgical opening, sufficient to prevent prolapse of iris tissue. Any such shields may be fabricated, and used, with or without retention flanges.

While the invention has been described supra with respect to use in a human eye, the iris shields disclosed herein can as well be used in animal eyes. For such uses, the inner diameter, the outer diameter, and the width of the shield will be specified and fabricated according to the sizes of the eyes to be treated.

Although the invention has been described with respect to various embodiments, it should be realized this invention is also capable of a wide variety of further and other embodiments within the spirit and scope of the appended claims.

Those skilled in the art will now see that certain modifications can be made to the apparatus and methods herein disclosed with respect to the illustrated embodiments, without departing from the spirit of the instant invention. And while the invention has been described above with respect to the preferred embodiments, it will be understood that the invention is adapted to numerous rearrangements, modifications, and alterations, and all such arrangements, modifications, and alterations are intended to be within the scope of the appended claims.

To the extent the following claims use means plus function language, it is not meant to include there, or in the instant specification, anything not structurally equivalent to what is shown in the embodiments disclosed in the specification.

Having thus described the invention, what is claimed is:

1. An iris shield for insertion through a surgical opening and into an anterior chamber of an eye during a surgery, such eye comprising an iris in such anterior chamber, such iris having an outer edge, an inner edge, and an iris width between the iris outer edge and the iris inner edge, said iris shield comprising:

a flexible biocompatible polymeric sheet, said sheet, and correspondingly said iris shield, having an anterior side and a posterior side, an inner edge extremity and an outer edge extremity, and a width (W) between the inner edge extremity and the outer edge extremity, said iris shield being suitable for being temporarily placed on such iris in such eye and to thereby overlie a substantial portion of the width of such iris, including being in direct contact with a central portion and an inner portion of the width of such iris, adjacent such surgical opening such that, when pressure inside such eye urges tissue of such iris toward such surgical opening during such surgery, said iris shield interferes with such iris tissue reaching such surgical opening, said iris shield being adapted and configured to be removed from such eye prior to completion of such surgery.

2. An iris shield as in claim 1 wherein said iris shield is in direct contact with substantially the entirety of the width of said iris proximate said surgical opening.

3. An iris shield as in claim 1, said sheet having an anterior surface for facing forwardly in such eye and a posterior surface for facing rearwardly in such eye, further comprising at least first and second retention flanges, spaced from each other and extending from the posterior surface adjacent the inner edge extremity of said polymeric sheet, rearwardly at one or more angles of from 30 degrees acute to the posterior surface of said sheet to 135 degrees obtuse to the posterior surface of said sheet.

4. An iris shield as in claim 1 wherein said iris shield engages the inner edges of such iris and prevents such iris from constricting over a pupil of such eye.

5. An iris shield as in claim 1 wherein said sheet has a Shore A durometer hardness of about 20 to about 75.

6. An iris shield as in claim 2, such sheet height being generally uniform across the width of said sheet between the inner edge extremity and the outer edge extremity, and such sheet height is about 100 microns to about 500 microns.

7. An iris shield as in claim 1 wherein said iris shield is moved, by such iris, against a cornea of such eye when pressure inside such eye, during such surgery, urges tissue of such iris toward such surgical opening, said iris shield thus shielding such iris tissue from the surgical opening.

8. An iris shield as in claim 3 wherein the inner edge extremity of said sheet generally overlies such inner edge of such iris of a such eye for which such iris shield is configured, when such iris is dilated, such that insertion of said iris shield into such eye, and engaging said iris shield with such inner edge of such iris of such eye, results in minimal, if any, retraction of such iris, and optionally stabilizes such iris against constriction of such iris.

9. An iris shield as in claim 3 wherein the inner edge extremity of said sheet generally aligns, at said retention flanges, with the inner edge of such iris of such eye for which such iris shield is configured, when such iris is dilated, such that insertion of said iris shield into an anterior chamber of such eye, and engaging said retention flanges with the inner edge of such iris of such eye, results in stabilizing such iris against constriction during such surgery.

10. An iris shield as in claim 1 wherein said sheet extends along a path selected from annular paths, "V"-shaped paths, and paths configured in shapes of polygons.

11. An iris shield as in claim 1, said shield further comprising at least third and fourth retention flanges extending from the anterior surface adjacent the inner edge extremity, frontwardly at one or more angles of from 30 degrees acute to the anterior surface to 135 degrees obtuse to the anterior surface.

12. An iris shield as in claim 11 wherein that portion of said iris shield which is in direct contact with such iris is wide enough adjacent such surgical opening to prevent such iris tissue from circumventing said iris shield and reaching the surgical opening.

13. An iris shield as in claim 1, said sheet, when at rest on an underlying flat supporting surface, having a generally flat top surface which extends from the inner edge extremity to the outer edge extremity.

14. An iris shield as in claim 1 wherein the width (W) of said iris shield, between the outer edge extremity and the inner edge extremity, is great enough to provide a shield effect to enough of such iris that any portion of the width of such iris which is not overlain by said iris shield is not susceptible to moving through such surgical opening when pressure inside such eye is raised during such surgery.

15. Use of an iris shield in an eye during a surgery, such eye having an iris, a pupil, and a cornea, said iris shield comprising:
a flexible biocompatible polymeric sheet, said sheet, and correspondingly said iris shield, having an inner edge extremity and an outer edge extremity, and a width (W) between the inner edge extremity and the outer edge extremity,
such use comprising inserting said iris shield through a surgical opening in an eye during such surgery, such iris having an outer edge, an inner edge, and an iris width between the iris outer edge and the iris inner edge,
said iris shield being disposed on such iris and overlying a substantial portion of the width of such iris, said iris shield being in direct contact with a central portion and an inner portion of such iris so as to prevent iris tissue from circumventing said iris shield such that, when pressure inside such eye urges tissue of such iris toward such surgical opening, said iris shield interferes with such iris tissue flowing out such surgical opening,
said iris shield being adapted and configured to be removed from such eye prior to completion of such surgery.

16. Use of an iris shield as in claim 15 wherein said iris shield is moved, by such iris, against the cornea when pressure inside such eye urges tissue of such iris toward such surgical opening.

17. Use of an iris shield as in claim 15 wherein said iris shield extends 360 degrees as a closed annulus about an axis of said sheet, on such iris.

18. Use of an iris shield as in claim 15 wherein that portion of said iris shield which is in direct contact with such iris is wide enough to prevent such iris tissue from circumventing said iris shield.

19. A method of treating a living eye during an ophthalmic surgery, the eye having an anterior chamber, and an iris in the anterior chamber, the iris having an outer edge and an inner edge, and a width between the outer edge and the inner edge, the method comprising:
(a) creating a surgical opening into the anterior chamber of the eye;
(b) inserting an iris shield into the eye through the surgical opening;
(c) positioning the iris shield on the iris such that the iris shield overlies a substantial portion of the width of the iris, including being in direct contact with a central portion, and an inner portion, of the width of the iris adjacent the surgical opening such that, when pressure inside the eye urges tissue of the iris toward the surgical opening, the iris shield interferes with such iris tissue reaching the surgical opening and prolapsing out of the eye;
(d) performing one or more surgical procedures while the iris shield is on the iris adjacent the surgical opening; and
(e) as part of completing the ophthalmic surgery, displacing the iris shield from over the iris.

20. A method as in claim 19, wherein the positioning of the iris shield in overlying relationship over the iris includes positioning the iris shield such that the iris shield is in direct contact with substantially the entirety of the width of such iris adjacent the surgical opening.

21. A method as in claim 19 wherein the width (W) of the iris shield, between the outer edge extremity and the inner edge extremity, is great enough to provide shield effect to enough of such iris that any portion of the width of such iris which is not in direct contact with the iris shield is not susceptible to moving through such surgical opening.

22. A method as in claim 19 wherein the iris shield is wide enough to prevent such iris tissue from circumventing the iris shield and reaching the surgical opening.

23. A method as in claim 19, such one or more additional surgical procedures including a procedure which results in the pressure inside the anterior chamber of the eye being raised, the iris shield being effective, when such pressure is so raised, to shield the iris from the effect of such increased pressure, sufficient to prevent prolapse of iris tissue out of the eye through a such respective surgical opening.

24. A method as in claim 19, the iris shield comprising a sheet having an anterior and a posterior, an inner edge extremity and an outer edge extremity, and first and second retention flanges, each such retention flange extending from a posterior surface of the sheet at the inner edge extremity, at an angle of from 30 degrees acute to the posterior surface of the sheet to 135 degrees obtuse to the posterior surface of the sheet, the method further comprising engaging at least one of such retention flanges with the inner edge of the iris, the iris shield thus engaging the inner edge of the iris.

25. A method as in claim 24, the iris shield preventing the iris from constricting during the surgical procedure.

26. A method as in claim 24 wherein the engaging of the retention flanges with the inner edge of the iris does not result in substantial retraction of the iris, optionally stabilizes the iris against constriction during the ophthalmic surgery.

27. A method as in claim 19 wherein the iris shield is in direct contact with substantially the entirety of the width of the iris proximate the surgical opening.

28. A method as in claim 19 wherein the iris shield overlies at least 75 percent of the width of the iris between the inner edge of the iris and the outer edge of the iris, including substantially overlying the outer edge of the iris.

29. A method as in claim 19 wherein the iris shield is positioned over the iris, and between the surgical opening and enough of that portion of the iris which is proximate the surgical opening, to prevent prolapse of iris tissue through the surgical opening.

30. An iris shield used in a method according to claim 19.

31. An iris shield used in a method according to claim 24.

32. An iris shield used in a method according to claim 27.

33. Use of an iris shield in an eye having an iris, a cornea, and a pupil, said iris shield comprising:

a flexible biocompatible polymeric sheet, said sheet, and correspondingly said iris shield, having an inner edge extremity and an outer edge extremity, and a width (W) between the inner edge extremity and the outer edge extremity, said iris shield having been inserted through a surgical opening into such eye during a surgical procedure, said iris shield being disposed on such iris and overlying a substantial portion of the width of such iris, said iris shield being in direct contact with a central portion and an inner portion of such iris adjacent the surgical opening so as to prevent tissue of such iris from circumventing said iris shield and reaching the surgical opening, said iris shield being adapted and configured to be removed from such eye prior to completion of such surgical procedure.

* * * * *